United States Patent [19]
Somberg

[11] Patent Number: 5,981,514
[45] Date of Patent: Nov. 9, 1999

[54] (N-ALKYL-N-HYDROXYMETHYLAMINO) ALKOXYBENZOYLBENZOFURANS AND THE PHOSPHATE ESTERS THEREOF

[76] Inventor: John C. Somberg, 25720 N. Saunders Rd., Lake Forest, Ill. 60045

[21] Appl. No.: 09/249,035

[22] Filed: Feb. 12, 1999

Related U.S. Application Data

[60] Provisional application No. 60/074,446, Feb. 12, 1998.

[51] Int. Cl.$^6$ ............... A61K 31/34; C07D 307/80; C07F 9/06
[52] U.S. Cl. ............... 514/100; 514/469; 549/220; 549/468
[58] Field of Search ............... 514/469, 100; 549/468, 220

[56] References Cited

U.S. PATENT DOCUMENTS

| | | |
|---|---|---|
| 3,248,401 | 4/1966 | Tondeur et al. |
| 4,235,871 | 11/1980 | Paphadjopoulos et al. |
| 4,501,728 | 2/1985 | Geho et al. |
| 4,737,323 | 4/1988 | Martin et al. |
| 4,837,028 | 6/1989 | Allen |
| 5,234,949 | 8/1993 | Ehrenpreis et al. |

OTHER PUBLICATIONS

Andreasen, F. et al., Pharmacokinetics of amiodarone after intravenous and oral administration, Eur. J. Clin. Pharmacol., 19(4):293–299 (1981).
Banitt, E.H. et al., Antiarrhythmics. 2. Synthesis and antiarrhythmic activity of N–(piperidylalkyl)trifluoroethoxybenzamides, J. Med. Chem., 20(6):821–826 (1977).
Bopp et al., Acute hemodynamic effects of intravenous amiodarone in patients with coronary artery disease, J. Cardio. Pharmacol., 7:286–289 (1985).
Casalini, C. et al., Metabolites and analogs of 2–ethyl–2, 3–dihydro–5–benzofuranacetic acid (furofenac): chemical and pharmacological properties, J. Pharm. Sci., 69(2):164–167 (1980).
Cullis, P.R. et al., Liposomes as Pharmaceuticals, Liposomes, Marc J. Ostro, ed., Marcel Dekker, Inc., New York, pp. 39–72 (1987).
Escoubet, B. et al., Suppression of Arrhythmias Within Hours After Single Oral Dose of Amiodarone and Relation to Plasma and Myocardial Concentrations, Am. J. Cardiol., 55:696–702 (1985).
Gough et al., Hypotensive Action of Commercial Intravenous Amiodarone and Polysorbate 80 in Dogs, Journal of Cardiovascular Pharmacology, 4:375–380 (1982).
Gregoriadis, Liposomes for drugs and vaccines, Trends in Biotechnology, 3(9):235–241 (1985).
Gruner, S.M., Materials Properties of Liposomal Bilayers, Liposomes, Marc J. Ostro, ed., Marcel Dekker, Inc., New York, pp. 1–38 (1987).
Kadish et al., The Use of Intravenous Amiodarone in the Acute Therapy of Life–Threatening tachyarrhythmias, Progress in Cardiovascular Diseases, 31:4, 281–294 (1989).
Kato, R. et al., Electrophysiologic effects of desethylamiodarone, an active metabolite of amiodarone: comparison with amiodarone during chronic administration in rabbits, Am. Heart J., 115(2):351–359 (1988).

Kodama, I. et al., Cellular electropharmacology of amiodarone. Cardiovasc. Res., 35(1):13–29 (1997).
Kosinzki, et al., Hemodynamic effects of intravenous amiodarone, J. Am. Coll. Card., 4:565–70 (1984).
Leppik, I.E. et al., Phenytoin prodrug: preclinical and clinical studies, Epilepsia, 30 Suppl. 2:S22–S26 (1989).
Morady et al., Intravenous Amiodarone in the Acute Treatment of Recurrent Symptomatic Ventricular Tachycardia, Am. J. Cardiol., 51:156–159 (1983).
Mostow et al., Rapid Suppression of Complex Ventricular Arrhythmias With High–Dose Oral Amiodarone, Circulation, 73:1231–1238 (1986).
Nattel, S., Pharmacodynamic studies of amiodarone and its active N–desethyl metabolite, J. Cardiovasc. Pharmacol., 8(4):771–777 (1986).
Nattel et al., The antiarrhythmic efficacy of amiodarone and desethylamiodarone, alone and in combination, in dogs with acute myocardial infarction, Circulation, 77(1):200–208 (1988).
Ortiz de Montellano, P.R., Biotransformations of Drugs and Chemicals, Molecular biology and biotechnology: a comprehensive desk reference, Meyers, VCH Publishers, New York, 117–120 (1995).
Physicians' Desk Reference, 1992, p. 2446 under tradename Cordarone(r).
Remington: Practice of The Science and Pharmacy, Gennaro, Mack Publishing, Eaton, 717–718, (1995).
Remington: Practice of The Science and Pharmacy, Gennaro, Mack Publishing, Eaton, 959 (1995).

(List continued on next page.)

*Primary Examiner*—Johann Richter
*Assistant Examiner*—Taofiq A. Solola
*Attorney, Agent, or Firm*—McDonnell, Boehnen, Hulbert & Berghoff

[57] ABSTRACT

Disclosed herein are compounds of the formula

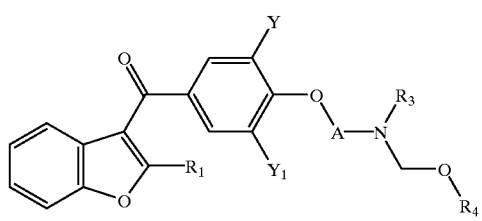

or the pharmaceutically acceptable salts thereof wherein
  $R_1$ is alkyl of 1–6 carbon atoms;
  A is alkylene having from 2–5 carbon atoms, each of which carbon atoms is substituted with $R_2$, where each $R_2$ is independently hydrogen or $C_1$–$C_6$ alkyl;
  $R_3$ is $C_1$–$C_6$ alkyl;
  Y and $Y_1$ are hydrogen or halogen; and
  $R_4$ is hydrogen or —$PO_3H$,
which compounds are water soluble and can be used for the treatment of arrhythmias.

17 Claims, No Drawings

OTHER PUBLICATIONS

Remme et al., Hemodynamic effects and tolerability of intravenous amiodarone in patients with impaired left ventricular function, Am. Heart J., 122:96–103 (1991).

Riva, E. et al., Anti–arrhythmic effects of amiodarone and desethylamiodarone on malignant ventricular arrhythmias arising as a consequence of ischaemia and reperfusion in the anaesthetised rat, Cardiovasc. Res., 23(4):331–339 (1989).

Saksena, S. et al., Clinical efficacy and electropharmacology of continuous intravenous amiodarone infusion and chronic oral amiodarone in refractory ventricular tachycardia, Am. J. Cardiol., 54(3):347–352 (1984).

Singh, B.N., Amiodarone: historical development and pharmacologic profile, Am. Heart J., 106(4 Pt 2):788–797 (1983).

Talajic, M. et al., Comparative electrophysiologic effects of intravenous amiodarone and desethylamiodarone in dogs: evidence for clinically relevant activity of the metabolite, Circulation, 75(1):265–271 (1987).

Torres–Arrault et al., Electrophysiologic effects of Tween 80 in the myocardium and specialized conduction system of the canine heart, Journal of Electrocardiology, 17(2):145–152 (1984).

Varia, S.A. et al., Phenytoin prodrugs III: water–soluble prodrugs for oral and/or parenteral use, J. Pharm. Sci., 73(8):1068–1073 (1984).

Varia, S.A. et al., Phenytoin prodrugs IV: Hydrolysis of various 3–(hydroxymethyl)phenytoin esters, J. Pharm. Sci., 73(8):1074–1080 (1984).

Varia, S.A. et al., Phenytoin prodrugs V: In vivo evaluation of some water–soluble phenytoin prodrugs in dogs, J. Pharm. Sci., 73(8):1080–1087 (1984).

Varia, S.A. et al., Phenytoin prodrugs VI: In vivo evaluation of a phosphate ester prodrug of phenytoin after parenteral administration to rats, J. Pharm. Sci., 73(8):1087–1090 (1984).

Venkatesh, N. et al., Effects of amiodarone and desethylamiodarone on rabbit myocardial beta–adrenoceptors and serum thyroid hormones—absence of relationship to serum and myocardial drug concentrations, J. Cardiovasc. Pharmacol., 8(5):989–997 (1986).

Wellens, H.J. et al., A comparison of the electrophysiologic effects of intravenous and oral amiodarone in the same patient, Circulation, 69(1):120–124 (1984).

Zhou, L. et al., Effects of amiodarone and its active metabolite desethylamiodarone on the ventricular defibrillation threshold, J. Am. Coll. Cardiol., 31(7):1672–1678 (1998).

(N-ALKYL-N-HYDROXYMETHYLAMINO) ALKOXYBENZOYLBENZOFURANS AND THE PHOSPHATE ESTERS THEREOF

REFERENCE TO RELATED APPLICATION

This application claims the benefit of U.S. Provisional Application S. No. 60/074,446, filed Feb. 12, 1998, which is incorporated by reference.

BACKGROUND OF THE INVENTION

1. Field of the Invention

The present invention relates to prodrugs of (N-alkylamino)alkoxybenzoylbenzofurans. More specifically, the invention relates to (N-alkyl-N-hydroxymethylamino)alkoxybenzoylbenzofurans and the phosphate esters thereof. It further relates to solutions, in particular parenteral solutions, of such prodrugs for use in the treatment of arrhythmia.

2. Description of the Related Art 2-n-Butyl-3-(3,5-diiodo-4-($\beta$-N-diethylaminoethoxy) benzoyl) benzofuran or 4-(2-(diethyl-amino)ethoxy)-3,5-diiodophenyl 2-butylbenzo[b]furan-3-yl ketone (hereinafter amiodarone) has been approved in an oral tablet form (CORDARONE®) for the treatment of life-threatening ventricular tachyarrhythmias in the United States since 1985. This drug is useful not only in treating these arrhythmias but also in treating less severe ventricular arrhythmias and many supraventricular arrhythmias including atrial fibrillation and reentrant tachyarrhythmias involving accessory pathways.

To treat arrhythmias, the compound may be administered in oral dosage forms such as in the form of a 200 mg tablet, or it may be administered in the form of an intravenous solution. See, for example, Escoubet, B. et al., "Suppression of Arrhythmias Within Hours After Single Oral Dose of Amiodarone and Relation to Plasma and Myocardial Concentrations", Am. J. Cardiol., (1985), 55:696–702, Mostow et al., "Rapid Suppression of Complex Ventricular Arrhythmias With High-Dose Oral Amiodarone", Circulation, (1986), 73:1231–8, Morady et al., "Intravenous Amiodarone in the Acute Treatment of Recurrent Symptomatic Ventricular Tachycardia", Am. J. Cardiol., (1983), 51:156–9 and Kadish et al. "The Use of Intravenous Amiodarone in the Acute Therapy of Life-Threatening Tachyarrhythmias", Progress in Cardiovascular Diseases, (1989), 31:4, 281–294.

Amiodarone is practically insoluble or slightly soluble in an aqueous solvent. Hence, it is difficult to formulate a dosage form suitable for intravenous administration. To aid the dissolution in water, for example, a surfactant has been suggested. Thus, the prior art intravenous dosage form for this compound, termed I.V. Cordarone, comprises amiodarone dissolved in a solvent comprising polysorbate 80 available under the tradename Tween-80, and benzyl alcohol. Prior art intravenous solutions of amiodarone will be designated IV Cordarone herein.

However, the use of this dosage form is highly undesirable because it exhibits deleterious cardiovascular effects attributable to the detergent. For example, Torres-Arrault et al. reported in Journal of Electrocardiology, 17 (2), 1984, pp 145–152, that Tween-80 is a potent cardiac depressant and causes hypotension in the dog. See also Gough et al., "Hypotensive Action of Commercial Intravenous Amiodarone and Polysorbate 80 in Dogs", Journal of Cardiovascular Pharmacology, (1982), 375–380. Further, Tween-80 is known to have anti-arrhythmic action. See Torres-Arrault, J. Electrocardiology, 17 (2), 1984, pp. 145–152, and Yasaka, et al., Cardiovascular Research 1979, 13: pp. 717–722.

Kosinzki, et al., Am. J. Cardiol., (1984) 4: 565–70, report that intravenous amiodarone (IV Cordarone) can result in significant impairment of left ventricular performance in patients with pre-existing left ventricular dysfunction. After acute intravenous bolus administration, patients with a left ventricular ejection fraction greater than 0.35 experienced improved cardiac performance due to both acute and chronic peripheral vasodilation. However, patients with a lower ejection fraction developed a 20% decrease in cardiac index and clinically significant elevation of right heart pressures after acute bolus administration.

Remme et al., Am. Heart J., (1991) 122: 96–103, report that intravenous amiodarone caused a 15% reduction in blood pressure and an 18% increase in heart rate, and a progressive reduction in contractility (V sub max) with a rise in left ventricular and diastolic pressure.

Bopp et al., J. Cardio. Pharmacol., (1985) 7: 286–289, report that IV Cordarone caused a decrease in the ejection fraction, an increase in pulmonary wedge pressure and a 15% decrease in dP/dt, and a 12% decrease in left ventricular work.

Each of the above three references discuss the effects of intravenous amiodarone (IV Cordarone), i.e., amiodarone solubilized for intravenous administration using polysorbate 80 and benzyl alcohol.

Both Tween 80 and benzyl alcohol have been required for dissolving amiodarone in prior art preparations. However, both Tween 80 and benzyl alcohol are known to cause hypotension, Munoz et al., European Heart Journal, (1988) 9: pp. 142–148; Varma, et al., Arzneim. Forsch (1985) 35(5), pp. 804–808. Also, the use of such prior art formulations in clinical studies has resulted in a clinically significant incidence of hypotension and resulting death. Scheinman, et al., Circulation (1995) 92: pp. 3264–3272; Levine et al. J. Am. Co. Cardiol. (1996) 27(1): 67–75; Mooss, et al., Am. J. Cardiol. (1990) 65: pp. 609–614; Kowey, et al., Circulation (1995) 92: pp. 3255–3263.

Further, Tween 80 is known to exert anti-arrhythmic action, as noted by Yasaka et. al., Cardiovascular Research (1979) 13: pp. 717–722.

U.S. Pat. No. 3,248,401, the disclosure of which is incorporated herein by reference in its entirety, issued Apr. 26, 1966 describes the preparation of 3-diethylaminoethoxybenzoyl benzofurans.

U.S. Pat. No. 5,234,949 discloses an amiodarone in acetate buffer formulation.

Physicians' Desk Reference, 1992, page 2446 under tradename Cordarone(r), provides the prescribing information relating to the oral form of this important product.

The Torres-Arrault, Taska and Gough articles described above set forth the hypotensive effects following intravenous administration of IV Cordarone (amiodarone in Tween-80).

The article "Intravenous Amiodarone", Clinical Progress in Electrophysiology and Pacing, (1986), 4:5, page 433, concludes that "Amiodarone, when administered intravenously, appears to have a rapid onset of action causing profound hemodynamic and electrophysiological effect."

SUMMARY OF THE INVENTION

The invention provides prodrugs in the form of phosphate esters of hydroxymethyl analogues of 4-(2-(N-diethylamino)alkhoxy)benzoyl)benzofurans. It also provides intermediates useful in the synthesis of the phosphate ester prodrugs. Thus, in a broad aspect, the invention provides compounds of formula I:

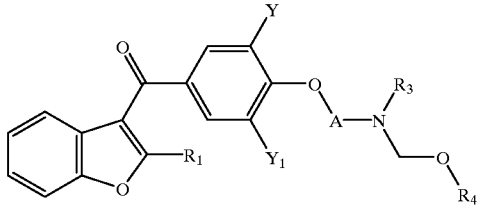

or the pharmaceutically acceptable salts thereof wherein $R_1$ is alkyl of 1–6 carbon atoms;

A is alkylene having from 2–5 carbon atoms, each of which carbon atoms is substituted with $R_2$, where each $R_2$ is independently hydrogen or $C_1$–$C_6$ alkyl;

$R_3$ is $C_1$–$C_6$ alkyl;

Y and $Y_1$ are hydrogen or halogen; and $R_4$ is hydrogen or —$PO_3H$.

Where $R_4$ in the compounds of formula I is —$PO_3H$, the compounds are water-soluble and can be used to produce aqueous solutions thereof suitable for parenteral administration. Such solutions can be conveniently manufactured, stored, and administered. The invention thus provides phosphate ester prodrug compounds and their water soluble salts that are readily hydrolyzed by the endogenous enzymes of the patient's body into effective anti-arrhythmic compounds. The invention thereby provides methods and compositions suitable for latentiation of (N-alkyl-N-hydroxymethylamino)alkoxybenzoylbenzofurans.

In a preferred aspect, the invention provides phosphate esters of 2-(N-alkyl-N-hydroxymethylamino) alkoxybenzoyl-benzofurans, i.e., compounds of formula I where $R_4$ is —$PO_3H$. In this aspect, the invention also provides water soluble salts of the phosphate esters of formula I. Such salts can be efficiently used to prepare aqueous solutions of the compounds for parenteral administration.

In another aspect, the invention provides hydroxymethyl products resulting from the hydrolysis of the phosphate ester prodrugs by phosphatases. These hydroxymethyl compounds are compounds of formula I where $R_4$ is hydrogen.

The phosphate esters of formula I are conveniently converted in vivo to the corresponding desethyl 2-(alkylamino)alkoxybenzoyl-benzofuran, i.e., an active compound having antiarrhythmic activity. See, e.g., Nattel, S, et al. (1988), Circulation, Vol. 77, No.1, pp. 200–208; Nattel, S, (1986) J. Cardiovasc Pharmacol, Vol. 8, No. 4, pp. 771–777; and Venkatesh, N, (1986) J. Cardiovasc Pharmacol, Vol. 8, No. 5, pp. 989–997. The 2-(alkylamino)alkoxybenzoyl-benzofuran compounds are known to be active metabolites of amiodarone which have antiarrhythmic activity. The phosphate ester prodrugs are conveniently used as the corresponding pharmaceutically acceptable salts of the phosphate ester. The prodrugs of the invention are water soluble and efficiently hydrolyzed to the active corresponding 2-(alkylamino)alkoxybenzoylbenzofuran by phosphatases in vivo.

In still another aspect, the invention provides compositions comprising aqueous solutions of pharmaceutically acceptable salts of the phosphate ester prodrug compounds.

Further, the invention provides methods for treating arrhythmia in mammalian patients comprising administering to the patient an effective amount of a prodrug compound of formula I. In these methods, the prodrug compound is typically administered as a composition comprising a solution of a salt of the prodrug compound in an aqueous vehicle. In preferred embodiments, the prodrug compound is administered intravenously as a composition comprising a solution of a salt of the prodrug compound in an aqueous vehicle.

In addition, the compounds of the invention have anti-arrhythmic activity, including type III antiarrhythmic activity. The compounds are therefore useful in treating arrhythmias in humans.

DETAILED DESCRIPTION OF THE INVENTION

In a broad aspect, the invention provides compounds of the formula:

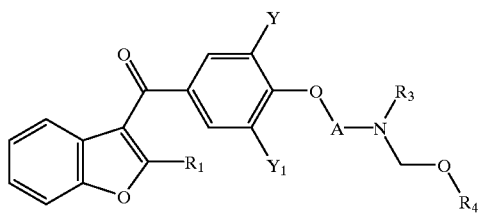

wherein $R_1$ is alkyl of 1–6 carbon atoms;

A is alkylene having from 2–5 carbon atoms, each of which carbon atoms is substituted with $R_2$, where each $R_2$ is independently hydrogen or $C_1$–$C_6$ alkyl;

$R_3$ is $C_1$–$C_6$ alkyl;

Y and $Y_1$ are hydrogen or halogen; and $R_4$ is hydrogen or —$PO_3H$.

The invention also provides compounds of formula III:

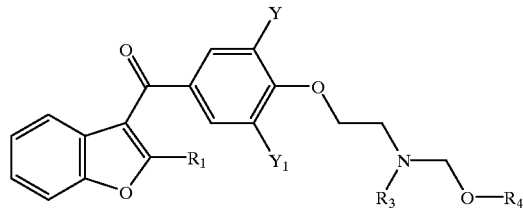

wherein $R_1$ is alkyl of 1–6 carbon atoms;

$R_3$ is $C_1$–$C_6$ alkyl;

Y and $Y_1$ are hydrogen or halogen; and $R_4$ is hydrogen or —$PO_3H$.

Preferred compounds of formula III are those where $R_1$ is $C_3$–$C_5$ alkyl; $R_3$ is $C_1$–$C_4$ alkyl, and Y and $Y_1$ are independently halogen. Other preferred compounds of formula III are those where Y and $Y_1$ are both iodo and $R_4$ is —$PO_3H$. Particularly preferred compounds of formula III are those where $R_1$ is $C_3$–$C_4$ alkyl; $R_3$ is ethyl, and Y and $Y_1$ are independently halogen; and $R_4$ is —$PO_3H$. The most preferred compounds of formula III are disodium, dipotassium, or diammonium salts of the corresponding parent compound.

In certain situations, compounds of formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by formula I, include, but are not limited to the compounds in Table I and their pharmaceutically acceptable base addition salts. Non-toxic pharmaceutical base addition salts include salts of bases such as sodium, potassium, calcium, ammonium, and the like. Those skilled in the art will recognize a wide variety of non-toxic pharmaceutically acceptable addition salts.

Unless otherwise indicated, "alkyl" or "lower alkyl" as used herein means straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkoxy" or "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentoxy, isopentoxy, neopentoxy, hexoxy, 2-hexoxy, 3-hexoxy, and 3-methylpentoxy.

By halogen in the present invention is meant fluorine, bromine, chlorine, and iodine.

Representative compounds of the invention are shown below in Table 1.

TABLE 1

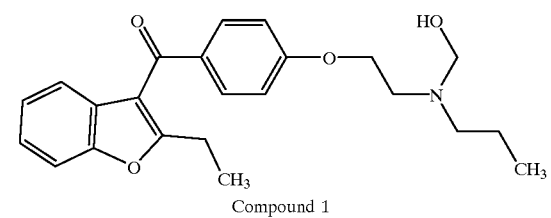

Compound 1

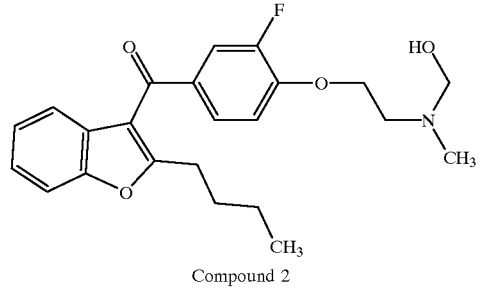

Compound 2

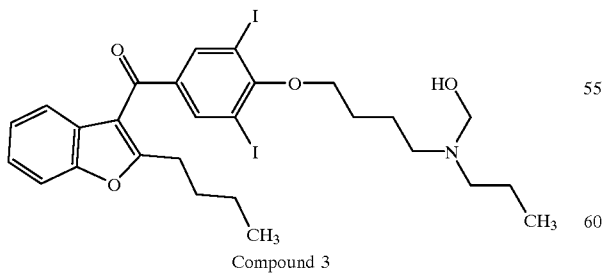

Compound 3

TABLE 1-continued

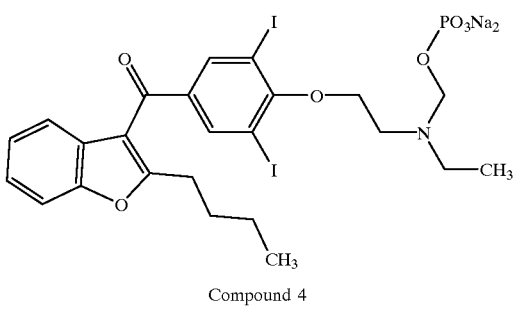

Compound 4

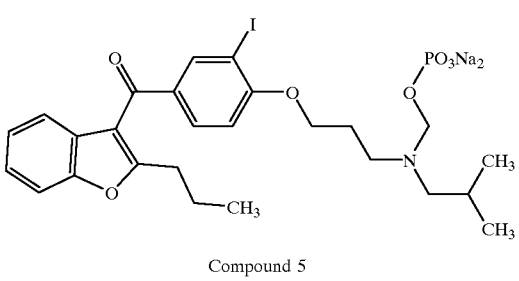

Compound 5

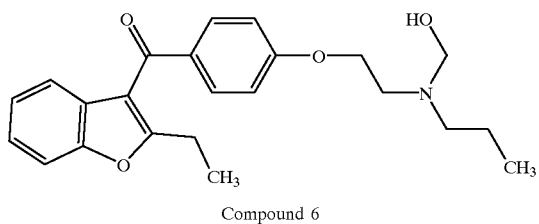

Compound 6

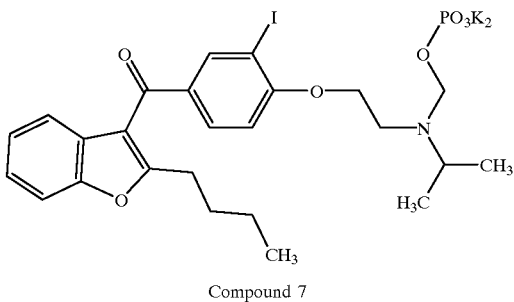

Compound 7

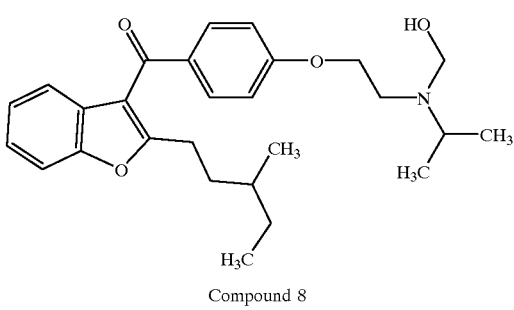

Compound 8

TABLE 1-continued

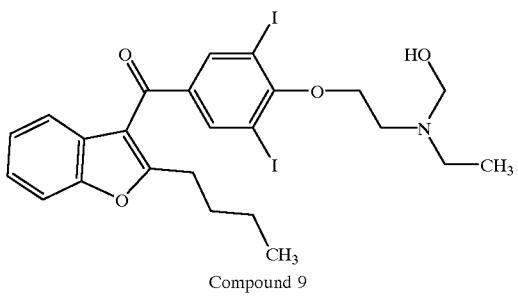

Compound 9

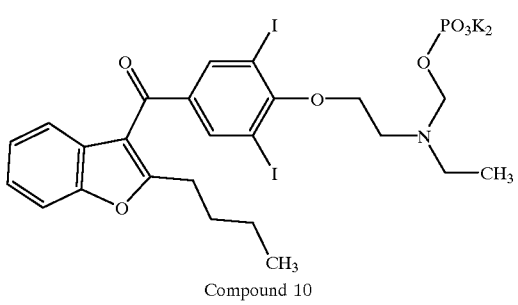

Compound 10

While the phosphate esters ($R_4$=—$PO_3H$) of the invention are water soluble, the salts of the phosphate esters are significantly more water soluble than the corresponding N,N-dialkyl compounds. Further, when administered to a mammal via an aqueous vehicle, e.g., water, the phosphate esters are advantageously hydrolyzed by endogenous phosphatases to yield the corresponding 2-(N-alkylamino)alkoxy benzoyl benzofuran as shown below in Scheme I. Scheme I depicts the hydrolysis of the disodium phosphate ester of the hydroxymethyl analogue of amiodarone, i.e., 2-n-butyl-3-(3,5-diiodo-4-(β-N-diethylaminoethoxy)benzoyl) benzofuran. This phosphatase hydrolysis yields the active metabolite of amiodarone, N-desethyl amiodarone or 2-n-butyl-3-(3,5-diiodo-4-(β-N-ethylaminoethoxy)benzoyl) benzofuran. Thus, the compounds of the invention (which have intrinsic antiarrhythmic activity) are prodrugs of compounds having Type III anti-arrhythmic activity.

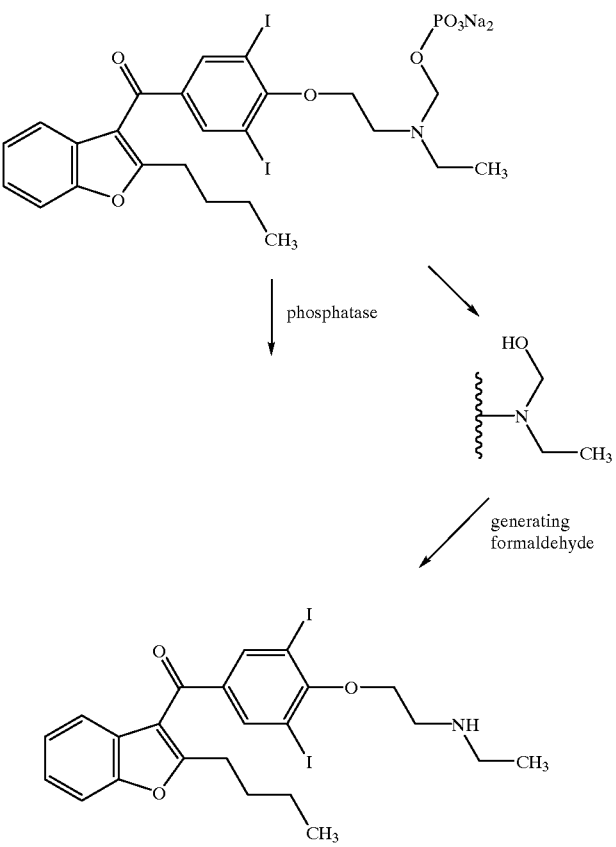

The compounds of formula I and their salts are suitable for the treatment of arrhythmia in mammalian patients, both in human and non-human animals and domestic pets, especially dogs and cats and farm animals such as sheep, swine and cattle. Preferably, a salt of a phosphate ester prodrug of formula I is administered parenterally to the patient as an aqueous solution to treat the arrhythmia.

While the preferred route of delivery is parenteral or intravenous administration, other methods of administering the compounds of formula I are acceptable. Consequently, other dosage forms of the compounds of the invention are suitable, as discussed herein.

The compounds of general formula I may be administered orally, topically, parenterally, by inhalation, by nasal or oral spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral, buccal or sublingual use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Alternatively, the compounds of the invention are encapsulated in liposomes. Liposomes are described widely in the literature and their structure is well known. See, e.g., Gregoriades, G., Trends in Biotechnology, (1985) 3(9) pp. 235–241, which is incorporated herein by reference. Liposomes are unilamellar or multilamellar lipid vesicles which enclose a fluid space or spaces. The walls of the liposomes are formed by a bilayer of one or more lipid components having polar heads and non-polar tails. In an aqueous (or polar) solution, the polar heads of one layer orient outwardly to extend into the surrounding medium, and the non-polar tail portions of the lipids associate with each other, thus providing a polar surface and a non-polar core in the wall of the liposome. Unilamellar liposomes have one such bilayer, whereas multilamellar liposomes generally have a plurality of substantially concentric bilayers.

A variety of methods are available for preparing liposomes are described in, e.g., U.S. Pat. Nos. 4,235,871, 4,501,728, 4,837,028; Gruner, S. M., "Materials Properties of Liposomal Bilayers," pp 1–38 in Marc J. Ostro, ed., Liposomes, Marcel Dekker, Inc., New York, (1987) and Cullis, P. R., et al., "Liposomes as Pharmaceuticals," pp 39–72 in Marc J. Ostro, ed., Liposomes, Marcel Dekker, Inc., New York, (1987), all of which are incorporated herein by reference. One method produces multilamellar vesicles of heterogeneous sizes. In this method, the vesicle-forming lipids are dissolved in a suitable organic solvent or solvent system and dried under vacuum or an inert gas to form a thin lipid film. Alternatively, the lipids may be dissolved in a suitable solvent, such as tertiary butanol, and then lyophilized to form a more homogeneous lipid mixture which is in a more easily hydrated powder-like form. This film or powder is covered with an aqueous buffered solution of a monovalent or divalent metal ion and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposomes through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. Liposomes having a size of from about 0.05 microns to about 0.15 microns are preferred.

Liposomes are recognized as useful for encapsulation of drugs and other therapeutic agents and for carrying these agents to selected in vivo sites. Drug administration via liposomes can result in reduced toxicity, altered tissue distribution, increased drug effectiveness, and an improved therapeutic index. Liposomes have also been used successfully for introducing various chemicals, biochemicals, genetic material and the like into viable cells in vitro, and as carriers for diagnostic agents.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the species of the host animal to be treated, the particular mode of administration, and the body weight of the host. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It will be convenient to formulate these animal feed and drinking water compositions with a pellet-dose of the drug so that the animal takes in an appropriate quantity of the composition along with its diet. It will also be convenient to present the composition as a premix for addition to the feed or drinking water.

Solutions of the phosphate ester salts of the invention typically comprise from about 10 mg/ml to about 50 mg/ml of compound. A more preferred concentration of the salt is from about 15 to 50 mg/ml.

The preferred methods of the invention employ bolus intravenous administration of from about 150 to 300 mg of prodrug dissolved in an aqueous media having the concentrations of components specified above.

In certain situations, the method will comprise intravenous administration of about 150 mg of prodrug as a single bolus dosage. Alternatively, and somewhat more preferably, the inventive method employs intravenous administration of about 300 mg of the prodrug in two 150 mg bolus dosages.

The solution thus formulated is indicated for the treatment of humans suffering from life-threatening, sustained ventricular tachycardia or fibrillation without the fear of the undesirable side effects observed with the administration of a solution of amiodarone in Tween-80.

An illustration of the preparation of compounds of the present invention is given in Scheme II.

Scheme II

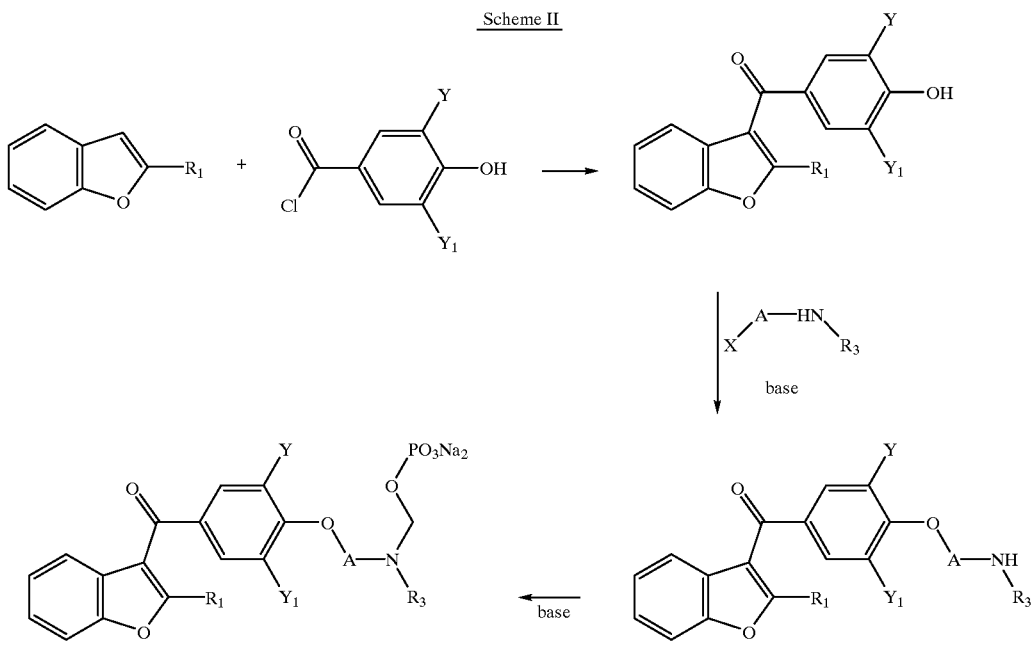

wherein $R_1$–$R_3$, A, Y and $Y_1$ are as defined above for formula I above, and X is a leaving group.

As outlined in the general method shown above in Scheme II for preparing compounds of the invention, a suitably substituted benzofuran, preferably 2-butylbenzofuran, is reacted with a suitably substituted benzoyl chloride in the presence of a Friedel-Crafts catalyst such as a Lewis acid or a proton acid. An excellent discussion of such catalysts appears in Olah, Friedel-Crafts and Related Reactions, Interscience Publ., New York, London and Sidney, 1963, Vol. I, Ch. III, and IV.

The acylation is carried out in a solvent, and any inert solvent which is not significantly attacked by the conditions may be used. For example, halogenated solvents such as methylene chloride, 1,2-dichloroethane, chloroform, and the like may be used, as can nonhalogenated solvents such as petroleum ether, hexane, and the like, and nitrohydrocarbons such as nitrobenzene and nitroalkanes.

The reaction may be carried out at temperatures from about ambient temperature to about 100° C., preferably at about the reflux temperature of the reaction mixture for processes catalyzed by proton acid catalysts, and preferably at about ambient temperature for Lewis acid catalyzed processes.

It is preferred to use a small molar excess of the Friedel-Crafts catalyst, i.e., from about 1.05 to 1.5, preferably 1.2, equivalents of the catalyst.

The resulting 3-substituted benzofuran is treated with a suitable base, such as, for example, sodium methoxide or sodium carbonate. The base is formed in situ by the addition of sodium to methanol or ethyl carbonate, respectively. Where methanol is used as the solvent, it is necessary to concentrate the reaction mixture and introduce toluene to the sodium salt formed of the intermediate phenol. A halogenated amine, for example, diethylaminoethylchloride, is then added to the reaction mixture and the reaction is typically stirred for 3–7 hours at elevated temperatures, preferably 90° C. After the mixture is allowed to cool to ambient temperature, it is repeatedly extracted with aqueous acid. The combined extracts are then basified and the desired product is subsequently extracted into an organic solvent, such as, for example, diethyl ether or ethyl acetate.

The O-alkylated product is then suspended in formalin and stirred at room temperature following the addition of a base, preferably potassium carbonate, and water. The desired N-desethyl hydroxy methyl compound is isolated out of the mixture. This compound is then treated with phosphorous trichloride in a suitable solvent, such as, for example, methylene chloride, and the reaction mixture is stirred at ambient temperature until completion of the reaction, usually about 2–7 hours. The product is isolated from the concentration of the organic layer after an aqueous base wash to afford the desired salt of the N-desethyl phosphate ester. If the sodium salt is desired, the aqueous base employed for the washing is sodium hydroxide. If the potassium salt is the target, the preferable base to use is potassium hydroxide. An overall quantitative yield of the desired salt of N-desethyl phosphate ester is typically obtained. Extensive methods for purification and isolation are not required.

The salts of the phosphate ester prodrugs are very soluble in aqueous media. This solubility facilitates the pharmaceutical utility of amiodarone for acute intravenous administration to patients with life-threatening conditions.

One skilled in the art will recognize that modifications may be made in the present invention without deviating from the spirit or scope of the invention. The invention is illustrated further by the following examples which are not to be construed as limiting the invention or scope of the specific procedures or compositions described herein.

EXAMPLE 1

The following compounds are prepared essentially according to the general procedure outlined in Scheme II and discussed above.

(a) 2-Butylbenzo[b]furan-3-yl 4-(2-(ethyl (hydroxymethyl)amino)ethoxy)-3,5-diiodophenyl ketone (Compound 9).

(b) 2-Butylbenzo[b]furan-3-yl 4-(2-(ethyl (hydroxymethyl)amino)ethoxy)-3,5-diiodophenyl ketone, disodium phosphate ester (Compound 4).

(c) 2-Butylbenzo[b]furan-3-yl 4-(2-(ethyl (hydroxymethyl)amino)ethoxy)-3,5-diiodophenyl ketone, dipotassium phosphate ester (Compound 10).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

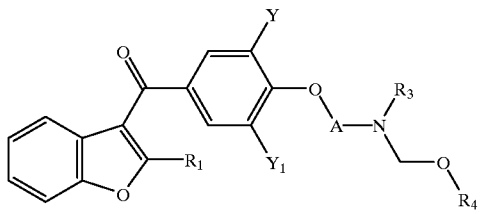

or the pharmaceutically acceptable salts thereof wherein $R_1$ is alkyl of 1–6 carbon atoms;

A is alkylene having from 2–5 carbon atoms, each of which carbon atoms is substituted with $R_2$, where each $R_2$ is independently hydrogen or $C_1$–$C_6$ alkyl;

$R_3$ is $C_1$–$C_6$ alkyl;

Y and $Y_1$ are hydrogen or halogen; and $R_4$ is hydrogen or —$PO_3H$.

2. A compound according to claim 1, wherein $R_2$ is hydrogen.

3. A compound according to claim 1, wherein Y and $Y_1$ are both halogen.

4. A compound according to claim 1, wherein $R_2$ is hydrogen and Y and $Y_1$ are both halogen.

5. A disodium salt of a compound according to claim 4.

6. A dipotassium salt of a compound according to claim 4.

7. A dipotassium salt of a compound according to claim 1.

8. A disodium salt of a compound according to claim 1.

9. A compound according to claim 1, wherein $R_4$ is hydrogen.

10. A compound according to claim 9, wherein Y and $Y_1$ are both halogen.

11. A compound according to claim 1, which is 2-butylbenzo[b]furan-3-yl 4-(2-(ethyl(hydroxymethyl)amino)ethoxy)-3,5-diiodophenyl ketone.

12. A compound according to claim 1, which is 2-butylbenzo[b]furan-3-yl 4-(2-(ethyl(hydroxymethyl)amino)ethoxy)-3,5-diiodophenyl ketone, disodium phosphate ester.

13. A compound according to claim 1, which is 2-butylbenzo[b]furan-3-yl 4-(2-(ethyl(hydroxymethyl)amino)ethoxy)-3,5-diiodophenyl ketone, dipotassium phosphate ester.

14. A composition suitable for parenteral administration to a mammal comprising a compound of the formula:

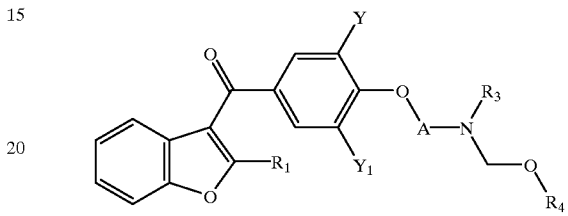

or the pharmaceutically acceptable salts thereof wherein $R_1$ is alkyl of 1–6 carbon atoms;

A is alkylene having from 2–5 carbon atoms, each of which carbon atoms is substituted with $R_2$, where each $R_2$ is independently hydrogen or $C_1$–$C_6$ alkyl;

$R_3$ is $C_1$–$C_6$ alkyl;

Y and $Y_1$ are hydrogen or halogen;

$R_4$ is hydrogen or —$PO_3H$;

and a pharmaceutically acceptable carrier.

15. The composition according to claim 14 wherein the compound is in aqueous solution.

16. The composition according to claim 14 wherein the compound is encapsulated in liposomes.

17. A method for treating arrhythmia in a patient having a need for such treatment comprising administering to the patient an effective amount of the composition according to claim 14.

* * * * *